US008178715B2

(12) United States Patent
Johnston et al.

(10) Patent No.: US 8,178,715 B2
(45) Date of Patent: May 15, 2012

(54) INTEGRATED PROCESS FOR THE PRODUCTION OF VINYL ACETATE FROM ACETIC ACID VIA ACETALDEHYDE

(75) Inventors: Victor J. Johnston, Houston, TX (US); James H. Zink, League City, TX (US); Laiyuan Chen, Houston, TX (US); Barbara F. Kimmich, League City, TX (US); Josefina T. Chapman, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 547 days.

(21) Appl. No.: 12/317,995

(22) Filed: Dec. 31, 2008

(65) Prior Publication Data

US 2010/0168466 A1    Jul. 1, 2010

(51) Int. Cl.
C07C 67/02 (2006.01)
C07C 69/72 (2006.01)

(52) U.S. Cl. .................................. 560/261; 560/205

(58) Field of Classification Search .................. None
See application file for complete search history.

(56) References Cited

U.S. PATENT DOCUMENTS

| 2,021,698 | A |   | 11/1935 | Perkins .................. 260/106 |
|---|---|---|---|---|
| 2,105,540 | A |   | 1/1938 | Lazier |
| 2,425,389 | A |   | 8/1947 | Oxley et al. ............. 260/491 |
| 2,859,241 | A |   | 11/1958 | Schnizer .................. 260/491 |
| 2,882,244 | A |   | 4/1959 | Milton ..................... 252/455 |
| 3,130,007 | A |   | 4/1964 | Breck ........................ 23/113 |
| 3,383,374 | A |   | 5/1968 | McTeer .................. 260/89.1 |
| 3,700,722 | A |   | 10/1972 | McTeer .................. 260/486 R |
| 3,702,886 | A |   | 11/1972 | Argauer et al. ............. 423/328 |
| 4,328,373 | A |   | 5/1982 | Strojny |
| 4,398,039 | A |   | 8/1983 | Pesa |
| 4,399,305 | A |   | 8/1983 | Schreck .................. 562/607 |
| 4,421,939 | A |   | 12/1983 | Kiff |
| 4,443,639 | A |   | 4/1984 | Pesa et al. |
| 4,550,185 | A |   | 10/1985 | Mabry |
| 4,613,700 | A |   | 9/1986 | Maki et al. ............... 568/435 |
| 4,620,050 | A |   | 10/1986 | Cognion et al. ........... 585/640 |
| 4,777,303 | A |   | 10/1988 | Kitson et al. |
| 4,804,791 | A |   | 2/1989 | Kitson et al. |
| 4,843,170 | A |   | 6/1989 | Isshiki et al. ............. 560/261 |
| 4,902,823 | A |   | 2/1990 | Wunder et al. |
| 4,978,778 | A |   | 12/1990 | Isshiki et al. |
| 4,978,779 | A |   | 12/1990 | Shawl et al. ............. 560/261 |
| 4,990,655 | A |   | 2/1991 | Kitson et al. |
| 5,137,861 | A |   | 8/1992 | Shih et al. |
| 5,149,680 | A |   | 9/1992 | Kitson et al. |
| 5,155,084 | A |   | 10/1992 | Horn et al. |
| 5,185,308 | A |   | 2/1993 | Bartley et al. |
| 5,227,517 | A | * | 7/1993 | Waller ..................... 560/238 |
| 5,243,095 | A |   | 9/1993 | Roberts et al. |
| 5,306,845 | A |   | 4/1994 | Yokohama et al. ......... 568/484 |
| 5,334,769 | A |   | 8/1994 | Ferrero et al. |
| 5,350,504 | A |   | 9/1994 | Dessau |
| 5,476,827 | A |   | 12/1995 | Ferrero et al. ............. 502/227 |
| 5,531,456 | A |   | 7/1996 | Riel ........................ 277/38 |
| RE35,377 | E |   | 11/1996 | Steinberg et al. ............. 518/704 |
| 5,585,523 | A |   | 12/1996 | Weiguny et al. |
| 5,674,800 | A |   | 10/1997 | Abel et al. |
| 5,691,267 | A |   | 11/1997 | Nicalau et al. |
| 5,719,315 | A |   | 2/1998 | Tustin et al. ............. 560/238 |
| 5,731,456 | A |   | 3/1998 | Tustin et al. |
| 5,821,111 | A |   | 10/1998 | Grady et al. ............. 435/252.5 |
| 5,945,570 | A |   | 8/1999 | Arhancet |
| 6,040,474 | A |   | 3/2000 | Jobson et al. |
| 6,049,008 | A |   | 4/2000 | Roberts |
| 6,114,571 | A |   | 9/2000 | Abel et al. |
| 6,121,498 | A |   | 9/2000 | Tustin et al. ............. 568/420 |
| 6,232,352 | B1 |   | 5/2001 | Vidalin .................. 518/700 |
| 6,476,261 | B2 |   | 11/2002 | Ellis et al. |
| 6,486,366 | B1 |   | 11/2002 | Ostgard |
| 6,495,730 | B1 |   | 12/2002 | Konishi |
| 6,657,078 | B2 |   | 12/2003 | Scates et al. ............. 562/519 |

(Continued)

FOREIGN PATENT DOCUMENTS

| EP | 0285420 | | 10/1988 |
|---|---|---|---|
| EP | 330853 | | 9/1989 |
| EP | 0372847 | | 6/1990 |
| EP | 0539274 | A1 | 4/1993 |
| EP | 0953560 | * | 11/1999 |
| EP | 0953560 | A1 | 11/1999 |
| EP | 1262234 | | 12/2002 |
| EP | 1277826 | | 1/2003 |
| EP | 2060555 | | 5/2009 |
| GB | 1168785 | | 10/1969 |

(Continued)

OTHER PUBLICATIONS

Pestman et al., Journal of Catalysis 168, 255-264 (1997).*
Ullmans Encyclopedia of Industrial Chemistry, 2005 Wiley-VCH Verlag GmbH & Co. KGaA, pp. 1-17.*

(Continued)

*Primary Examiner* — Karl J Puttlitz
(74) *Attorney, Agent, or Firm* — Roberts Mlotkowski Safran & Cole, P.C.

(57) ABSTRACT

This invention provides an integrated multistep economical process for the production of vinyl acetate monomer (VAM) from acetic acid in the vapor phase. First, acetic acid is selectively hydrogenated over a hydrogenating catalyst composition to form acetaldehyde. Acetaldehyde so formed can be converted to ethylidene diacetate via reaction with acetic anhydride. In a subsequent step so formed ethylidene diacetate is thermally decomposed to form VAM and acetic acid. Alternatively, acetaldehyde formed in the first step can selectively be reacted with ketene to form VAM. In an embodiment of this invention reaction of acetic acid and hydrogen over platinum and iron supported on silica selectively produces acetaldehyde in a vapor phase at a temperature of about 300° C., which is selectively hydrogenated over platinum supported catalyst to form ethanol and dehydrated over NAFION catalyst to form ethylene at a temperature of about 185° C., which is mixed with molecular oxygen, acetic acid and reacted over a palladium/gold/potassium catalyst supported on titania to form VAM at a temperature of about 150° C. to 170° C.

8 Claims, No Drawings

U.S. PATENT DOCUMENTS

| | | | |
|---|---|---|---|
| 6,685,754 B2 | 2/2004 | Kindig et al. | 48/210 |
| 6,696,596 B1 | 2/2004 | Herzog et al. | |
| 6,852,877 B1 | 2/2005 | Zeyss et al. | |
| 7,084,312 B1 | 8/2006 | Huber | |
| 7,425,657 B1 | 9/2008 | Elliott et al. | |
| 7,538,060 B2 | 5/2009 | Barnicki et al. | |
| 7,816,565 B2 | 10/2010 | Johnston | |
| 2006/0106246 A1 | 5/2006 | Warner et al. | |
| 2010/0029993 A1* | 2/2010 | Johnston et al. | 568/484 |
| 2010/0069515 A1 | 3/2010 | Tirtowidjojo | |
| 2010/0168466 A1 | 7/2010 | Johnston | |
| 2011/0004026 A1* | 1/2011 | Johnston et al. | 568/484 |
| 2011/0251435 A1* | 10/2011 | Johnston et al. | 568/484 |
| 2011/0263891 A1* | 10/2011 | Weiner et al. | 560/265 |

FOREIGN PATENT DOCUMENTS

| | | |
|---|---|---|
| GB | 2 136 704 A | 9/1987 |
| WO | 99/08791 | 2/1999 |
| WO | 2005/102513 | 11/2005 |
| WO | 2009/105860 | 3/2009 |
| WO | 2009/086839 | 7/2009 |
| WO | 2010014145 | 2/2010 |
| WO | 2010014153 | 2/2010 |

OTHER PUBLICATIONS

Brunauer Emmett and Teller J. Am. Chem. Soc. 60,309 (1938); Proc. Roy. Soc. A314, pp. 473-498; and Mol. Sieves Pap. Conf., 1967, 78, Soc. Chem. Ind. London, by D. Domine and J. Quobex.

U.S. Appl. No. 12/221,135, filed Jul. 31, 2008, Johnston et al.

Zheng, et al. (2007). Preparation and catalytic properties of a bimetallic Sn—Pt complex in the supercages of NaY zeolite by use of surface organometallic chemistry, Applied Organometallic Chemistry, 21(10), 836-840.

Tustin et al. Synthesis of vinyl acetate monomer from synthesis gas, Catalyst Today, vol. 58(4) (2000) pp. 281-291.

Santori et al. (2000). Hydrogenation of carbonylic compounds on Pt/SiO2 catalysts modified with SnBu4, Studies in Surface Science and Catalysis, 130, 2063-2068.

Roscher, "Ullmann's Encyclopedia of Industrial Chemistry—Vinyl Esters," Ullmann's Encyclopedia of Industrial Chemistry (2000) p. 1-18.

Pestman et al., The formation of ketones and aldehydes from carboxylic acids, structure-activity relationship for two competitive reactions, Journal of Molecular Catalysis A: Chemical 103 Jun. 14, 1995, 175-180.

Acala, et al., (2005). Experimental and DFT studies of the conversion of ethanol and acetic acid on PtSn-based catalysts, Journal of Physical Chemistry, 109(6), 2074-2085.

International Search Report and Written Opinion for PCT/US2009/004187 mailed Mar. 24, 2010 (14 pages).

Pestman et al., Reactions of Carboxylic Acids on Oxides, Journal of Catalysis 168:255-264 (1997).

Pestman et al., Identification of the Active Sites in the Selective Hydrogenation of Acetic Acid to Acetaldehyde on Iron Oxide Catalysts, Journal of Catalysis 174:142-152 (1998).

* cited by examiner

INTEGRATED PROCESS FOR THE PRODUCTION OF VINYL ACETATE FROM ACETIC ACID VIA ACETALDEHYDE

FIELD OF THE INVENTION

The present invention relates generally to an integrated process for the production of vinyl acetate monomer (VAM) from acetic acid via acetaldehyde. More specifically, the present invention relates to an integrated process first involving hydrogenating acetic acid utilizing a catalyst composed of a supported metal catalyst, such as, for example, iron, platinum or ruthenium supported on a suitable catalyst support optionally including one or more additional hydrogenating metals to form acetaldehyde with high selectivity. In a subsequent second step, the acetaldehyde thus formed is converted to ethylidene diacetate through a conversion reaction with acetic anhydride. The ethylidene diacetate is then thermally decomposed to VAM and acetic acid. This invention also relates to a process for the direct conversion of acetaldehyde to VAM by reaction with ketene.

BACKGROUND

There is a long felt need for an economically viable process to form VAM directly from acetic acid. VAM is an important monomer in the production of polyvinyl acetate and polyvinyl alcohol products among other important uses. VAM is currently produced from two key raw materials, ethylene and acetic acid. Ethylene is predominantly produced from petroleum based raw materials although acetic acid can be produced to a lesser extent from petroleum based raw materials. Therefore, fluctuating natural gas and crude oil prices contribute to fluctuations in the cost of conventionally produced, petroleum or natural gas-sourced VAM, making the need for alternative sources of VAM all the greater when oil prices rise.

It has now been found that VAM can be produced essentially from a mixture of carbon monoxide and hydrogen (commonly known as synthesis gas or syn gas) involving a few industrially viable steps. For example, it is well known that synthesis gas can be reduced to methanol, which is in fact the industrially preferred way to manufacture methanol. Methanol thus formed can then be converted selectively to acetic acid under catalytic carbonylation conditions, which is again the industrially preferred process for the manufacture of acetic acid. The acetic acid thus formed then can be selectively converted to acetaldehyde under suitable catalytic conditions. The thus formed acetaldehyde along with acetic anhydride are reacted and converted to ethylidene diacetate which is subsequently thermally decomposed to VAM and acetic acid. Although there are no known preferred processes for such a conversion, the prior art does provide certain processes for such a conversion of acetic acid to acetaldehyde albeit at low conversions and yields thus making it industrially unsuitable.

For instance, the catalytic hydrogenation of aromatic carboxylic acids to produce aromatic aldehydes has been reported in the literature. For example, U.S. Pat. No. 4,613,700 to Maki et al. discloses that aromatic aldehydes can be formed from aromatic carboxylic acids using a catalyst comprising zirconium oxide containing as an essential component at least one element selected from the group consisting of chromium, manganese, iron, cobalt, zinc, bismuth, lead rhenium and the elements of Group III in periods 3 to 6 of the periodic table. However, no examples of catalytic hydrogenation of aliphatic carboxylic acids such as acetic acid are provided in this disclosure.

U.S. Pat. No. 5,306,845 to Yokohama et al. discloses a method of producing an aldehyde, which comprises hydrogenating a carboxylic acid or its alkyl ester with molecular hydrogen in the presence of a catalyst containing chromium oxide of high purity having a specific surface area of at least 10 $m^2/g$ and a total content of sodium, potassium, magnesium and calcium of not more than 0.4 weight percent. It is further reported therein that the hydrogenation reaction is conducted while maintaining the carboxylic acid or its alkyl ester at a concentration of not more than 10 volume percent. Additionally, the only example reported therein is hydrogenation of stearic acid to stearyl aldehyde. Most importantly, the selectivity to aldehyde drops significantly even if the total content of sodium, potassium, magnesium and calcium increases from about 0.3 weight percent to about 0.46 weight percent, thus rendering the process not suitable for a commercial operation.

U.S. Pat. No. 5,476,827 to Ferrero et al. describes a process for the preparation of aldehydes by catalytic hydrogenation of carboxylic acids, esters or anhydrides utilizing a bimetallic ruthenium/tin catalyst. The preferred carboxylic acids are the α-β-unsaturated carboxylic acids with an aromatic back bone or aromatic carboxylic acids. No examples of aliphatic carboxylic acids including acetic acid are provided.

U.S. Pat. No. 6,121,498 to Tustin et al. discloses a method for producing acetaldehyde from acetic acid. In this process, acetic acid is hydrogenated with hydrogen at an elevated temperature in the presence of an iron oxide catalyst containing between 2.5 and 90 weight percent palladium. However, the optimal condition reported therein is comprised of an iron oxide catalyst containing at least about 20 weight percent palladium, which affords about 80 percent selectivity to acetaldehyde with about 50 percent conversion of acetic acid. Additionally, significant amounts of by-products including methane, ethane, ethylene, ethanol and acetone are formed.

The acetaldehyde so formed may selectively be reacted with acetic anhydride to form ethylidene diacetate first and subsequent thermal decomposition of the ethylidene diacetate to VAM and acetic acid.

For example, U.S. Pat. No. 2,021,698 to Perkins teaches a process for making vinyl esters, such as vinyl acetate, by reacting acetic anhydride with paraldehyde and sulfuric acid. There is no teaching of making ethylidene diacetate first and then thermally decomposing said diacetate in order to obtain vinyl acetate and acetic acid. Perkins teaches away from the use of an intermediate product, such as ethylidene diacetate to arrive at vinyl acetate.

U.S. Pat. No. 4,843,170 to Isshiki et al. discloses a process for producing vinyl acetate from methanol wherein the methanol is converted to ethanol, methyl acetate, dimethylacetal, and acetaldehyde. The methyl acetate is further processed through carbonylation to form acetic anhydride which is mixed with the dimethylacetal and acetaldehyde from the methanol conversion step. The acetic anhydride, dimethylacetal and acetaldehyde are reacted to form ethylidene diacetate, which is thermally decomposed to form VAM and acetic acid. This multi-step process includes more stages than the process of the present invention in order to produce acetaldehyde.

U.S. Pat. No. 4,978,778 to Isshiki et al. also discloses a process for producing vinyl acetate wherein the acetic anhydride is reacted with hydrogen in the presence of a catalyst instead of acetaldehyde. As the described process converts vinyl acetate directly from acetic anhydride and hydrogen, there is no need to produce ethylidene diacetate in order to form VAM through thermal decomposition which is the basis for the present invention.

Alternatively, acetaldehyde may also be reacted with a ketene to form VAM. For instance, U.S. Pat. Nos. 5,719,315 and 5,531,456 both to Tustin et al. disclose processes for the preparation of vinyl acetate wherein acetaldehyde is mixed with a ketene and the mixture is subsequently contacted with a catalyst in a contact zone.

From the foregoing it is apparent that the existing processes do not have the requisite selectivity to form acetaldehyde directly from acetic acid and then react so formed acetaldehyde and acetic anhydride selectively to form ethylidene diacetate with further conversion through thermal decomposition to VAM and acetic acid in an integrated process thus making them industrially adoptable to produce VAM essentially from synthesis gas and/or synthesis gas based products.

SUMMARY OF THE INVENTION

Surprisingly, it has now been unexpectedly found that VAM can be produced on an industrial scale involving an integrated process by which acetaldehyde is first formed directly from acetic acid with very high selectivity and yield, which is subsequently reacted with acetic anhydride to form ethylidene diacetate which is thermally decomposed to form VAM and acetic acid in the presence of a suitable catalyst. More particularly, this invention provides a process for the selective formation of VAM from acetic acid comprising: (a) hydrogenating acetic acid in the presence of hydrogen over a first hydrogenating catalyst comprising at least one metal selected from the group consisting of iron, copper, gold, platinum, palladium and ruthenium supported on a suitable catalyst support. Optionally, the catalyst is further comprised of one or more metal catalysts selected from the group consisting of tin, aluminum, potassium, cobalt, molybdenum, tungsten and vanadium to form a first gaseous product stream; (b) enriching said first gaseous product stream with acetaldehyde at least up to 50 mole percent; (c) reacting said enriched first gaseous product stream from step (b) with acetic anhydride in a second reaction zone to form a second gaseous product stream consisting essentially of ethylidene acetate; (d) thermally decomposing said second gaseous product stream from step (c) over a suitable catalyst to form a third gaseous product stream consisting essentially of VAM and acetic acid; and (e) separating vinyl acetate from said third gaseous product stream.

In another embodiment of this invention, this invention provides a process for the selective formation of VAM from acetic acid comprising: (a) hydrogenating acetic acid in the presence of hydrogen over a first hydrogenating catalyst comprising at least one metal selected from the group consisting of iron, copper, gold, platinum, palladium and ruthenium supported on a suitable catalyst support. Optionally, the catalyst is further comprised of one or more metal catalysts selected from the group consisting of tin, aluminum, potassium, cobalt, molybdenum, tungsten and vanadium to form a first gaseous product stream; (b) enriching said first gaseous product stream with acetaldehyde at least up to 50 mole percent; (c) reacting said enriched first gaseous product stream from step (b) with acetic anhydride in a second reaction zone to form a second gaseous product stream consisting essentially of ethylidene diacetate; (d) thermally decomposing said second gaseous product stream from step (c) over a suitable cracking catalyst to form a third gaseous product stream consisting essentially a mixture of VAM and acetic acid; and (e) separating vinyl acetate from said third gaseous product stream.

In yet another embodiment of this invention there is also provided a process for the selective formation of VAM from acetic acid comprising: (a) hydrogenating acetic acid in the presence of hydrogen over a first hydrogenating catalyst comprising at least one metal selected from the group consisting of iron, copper, gold, platinum, palladium and ruthenium supported on a suitable catalyst support. Optionally, the catalyst is further comprised of one or more metal catalysts selected from the group consisting of tin, aluminum, potassium, cobalt, molybdenum, tungsten and vanadium to form a first gaseous product stream; (b) enriching said first gaseous product stream with acetaldehyde at least up to 50 mole percent; (c) reacting said enriched first gaseous product stream from step (b) with ketene in a second reaction zone to form a second gaseous product stream comprising vinyl acetate; and (e) separating vinyl acetate from said second gaseous product stream.

More specifically, the catalyst for the selective formation of acetaldehyde in the first step of the process of this invention is typically comprised of supported ruthenium alone or in combination with tin or iron; a supported iron alone or in combination with platinum or cobalt; or a combination of platinum and tin. Similarly, other catalysts suitable in the process of this invention include supported palladium alone or a combination of palladium/gold (Pd/Au) or palladium/copper (Pd/Cu), which can further comprise potassium acetate. Also, suitable catalysts are a combination of palladium/iron (Pd/Fe), iron/cobalt (Fe/Co), copper/molybdenum (Cu/Mo) or copper/aluminum (Cu/Al). Suitable catalyst supports include without any limitation, silica, alumina, calcium silicate, carbon, zirconia, zirconia-silica, titania, titania-silica, iron oxide and zeolite catalysts such as for example H-ZSM-5. Silica and iron oxide are particularly preferred catalyst supports in the process of this invention.

DETAILED DESCRIPTION OF THE INVENTION

The invention is described in detail below with reference to numerous embodiments for purposes of exemplification and illustration only. Modifications to particular embodiments within the spirit and scope of the present invention, set forth in the appended claims, will be readily apparent to those of skill in the art.

Unless more specifically defined below, terminology as used herein is given its ordinary meaning. Mole percent (mole % or %) and like terms refer to mole percent unless otherwise indicated. Weight percent (wt % or %) and like terms refer to weight percent unless otherwise indicated.

Typically, the catalyst metal loadings are expressed as weight percent of a catalyst metal based on the total dry weight of the metal and catalyst support. Thus, for example, one (1) weight percent of metal on a support means that one gram of pure metal is present in 100 grams of supported metal catalyst, i.e., the combined weight of support (99 grams) and the metal (1 gram).

"Conversion" is expressed as a mole percentage based on acetic acid in the feed. The conversion of acetic acid (AcOH) is calculated from gas chromatography (GC) data using the following equation:

$$\text{AcOH conversion}(\%) = 100 * \frac{\text{mmol AcOH in (feed stream)} - \text{mmol AcOH out } (GC)}{\text{mmol AcOH in (feed Stream)}}$$

"Selectivity" is expressed as a mole percent based on converted acetic acid. For example, if the conversion is 50 mole % and 50 mole % of the converted acetic acid is converted to ethyl acetate (EtOAC), we refer to the ethyl acetate selectivity as 50%. Selectivity is calculated from gas chromatography (GC) data using the following equation:

Selectivity to EtOAc =

$$100 * \frac{\text{mmol EtOAc out } (GC)}{\frac{\text{Total mmol C out } (GC)}{2} - \text{mmol AcOH out } (GC)}$$

wherein "Total mmol C out (GC)" refers to total mmols of carbon from all of the products analyzed by gas chromatograph.

The reaction proceeds in accordance with the following chemical equations:

a) Hydrogenation of Acetic Acid to Acetaldehyde

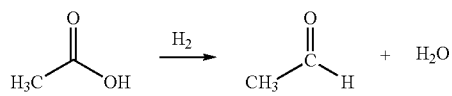

b) Addition of Acetaldehyde and Acetic Anhydride to Form Ethylidene Diacetate

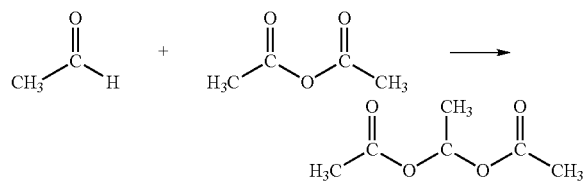

c) Thermal Decomposition of Ethylidene Diacete to Form VAM and Acetic Acid

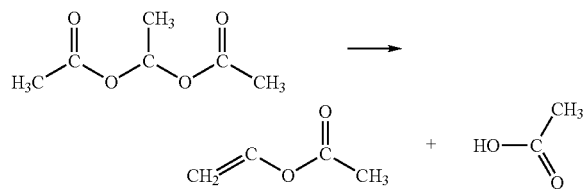

d) Pyrolysis of Acetic Acid to Form Ketene

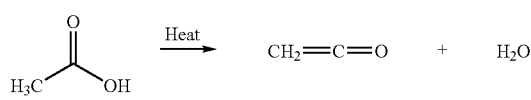

e) Addition of Ketene to Acetaldehyde to Form VAM

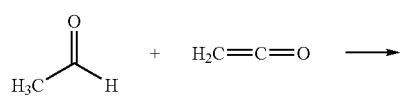

-continued

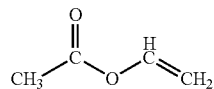

Hydrogenation of Acetic Acid to Acetaldehyde:

In accordance with the invention, conversion of acetic acid to acetaldehyde can be carried out in a variety of configurations, such as for example, in a single reaction zone which may be a layered fixed bed, if so desired. An adiabatic reactor could be used, or a shell and tube reactor provided with a heat transfer medium could be used. The fixed bed can comprise a mixture of different catalyst particles or catalyst particles which include multiple catalysts as further described herein. The fixed bed may also include a layer of particulate material making up a mixing zone for the reactants. A reaction mixture including acetic acid, hydrogen and optionally an inert carrier gas is fed to the bed as a stream under pressure to the mixing zone. The stream is subsequently supplied (by way of pressure drop) to the reaction zone or layer. Reaction zone comprises a catalytic composition including a suitable hydrogenating catalyst where acetic acid is hydrogenated to produce acetaldehyde. Any suitable particle size may be used depending upon the type of reactor, throughput requirements and so forth.

Although various metal supported hydrogenating catalysts known to one skilled in the art can be employed in hydrogenating acetic acid to form acetaldehyde in the process of this invention it is preferred that the hydrogenating catalyst employed contains at least one or more metals selected from the group consisting of iron, copper, gold, platinum, palladium and ruthenium supported on a suitable catalyst support. Optionally, a second or third metal can be selected from the group consisting of tin, aluminum, potassium, cobalt, molybdenum, tungsten and vanadium. Preferably, the catalyst suitable for the process of this invention is comprised of ruthenium alone, supported on a suitable support such as iron oxide or silica or a combination of ruthenium and tin or ruthenium and iron supported on a suitable catalyst support. Similarly, the preferred hydrogenation catalyst is iron alone supported on a suitable support such as silica or a combination of iron and platinum or a combination of iron and cobalt supported on a suitable catalyst support such as silica. Similarly, other catalysts suitable in the process of this invention include supported palladium alone or a combination of palladium/ gold (Pd/Au) or palladium/copper (Pd/Cu), which can further comprise potassium acetate. Also suitable catalysts are a combination of palladium/iron (Pd/Fe), iron/cobalt (Fe/Co), copper/molybdenum (Cu/Mo) or copper/aluminum (Cu/Al).

Typically, when bimetallic catalysts are employed it is preferred that a suitable weight ratio of a combination of metals on a suitable support can be used as a hydrogenating catalyst. Thus, for example, a combination of ruthenium and iron (Ru/Fe), ruthenium and tin (Ru/Sn), palladium/copper (Pd/Cu), palladium/iron (Pd/Fe) in the weight ratio of about 0.1-1 are particularly preferred. More preferably, a weight ratio of Ru/Fe or Ru/Sn or Pd/Cu or Pd/Fe is about 0.2-0.5 and most preferably the weight ratio of Ru/Fe or Ru/Sn or Pd/Cu or Pd/Fe is about 0.2. Similar weight ratios can be employed for a catalyst combination of platinum and iron Pt/Fe, i.e., a weight ratio of 0.1-1, preferably 0.2-0.5 and most preferably 0.2. When a combination of cobalt and iron (Co/Fe) or copper/molybdenum (Cu/Mo) or copper/aluminum (Cu/Al) supported on a suitable catalyst support is employed, the preferred weight ratio of Co/Fe or Cu/Mo or Cu/Al is in the range of 1 to 5. For instance, a combination of 17.4 weight percent of cobalt and 4.8 weight percent of iron supported on silica is commercially available. Similarly, a copper-aluminum catalyst is sold under the name of T-4489 by Sud Chemie.

When ruthenium alone or palladium alone or iron alone is used as the metal catalyst on a suitable support any loading level of ruthenium, palladium or iron can be employed so as to affect the selective hydrogenation of acetic acid to acetaldehyde. Typically, however, the ruthenium or palladium loading level can range from 0.5 weight percent to about 20 weight percent, preferably 1 weight percent to about 10 weight percent and most preferably 1 weight percent to about 5 weight percent. Generally when a noble metal such as ruthenium or palladium alone are employed in the process of this invention, 0.5 to 1 weight percent of catalyst metal may be sufficient to obtain the optimum catalytic benefit. Preferred catalyst supports for ruthenium or palladium are iron oxide or silica. Similarly, when iron alone is used as the metal catalyst, the loading level of iron can range from 1 weight percent to about 20 weight percent, preferably 2 weight percent to about 10 weight percent and most preferably 3 weight percent to about 8 weight percent. Preferred catalyst support for iron is silica.

When bimetallic catalysts employed are two noble metals such as palladium and gold then the metal loading of each of the noble metal loading is in the range of from about 0.5 weight percent to about 20 weight percent, preferably 1 weight percent to about 10 weight percent and most preferably 1 weight percent to about 5 weight percent. However, as already noted above, low loadings of about 0.5 weight percent or 1 weight percent of each of the noble metals, such as palladium or gold brings about optimum catalytic effect in the process of this invention.

Various catalyst supports known in the art can be used to support the catalysts of this invention. Examples of such supports include without any limitation, zeolite, such as H-ZSM-5, iron oxide, silica, alumina, titania, zirconia, magnesium oxide, calcium silicate, carbon, graphite and a mixture thereof. Preferred supports are silica and iron oxide. More preferably silica is used as a catalyst support in the process of this invention. It is also important to note that the higher the purity of silica, the better it is as a support. Various forms of commercially available silica supports can be used in this invention including high surface area silica (HSA silica) as well as low surface area silica (LSA silica).

In another aspect of the process of this invention, any of known the zeolite catalysts can also be employed as a catalyst support. While any zeolite having a pore diameter of at least about 0.6 nm can be used, preferably employed among such zeolites are the catalyst supports selected from the group consisting of mordenites, ZSM-5, a zeolite X and a zeolite Y.

The preparation of large-pore mordenites is described, for example, in U.S. Pat. No. 4,018,514 to Plummer and in Mol. Sieves Pap. Conf., 1967, 78, Soc. Chem. Ind. London, by D. DOMINE and J. QUOBEX.

Zeolite X is described, for example, in U.S. Pat. No. 2,882,244 to Milton and zeolite Y in U.S. Pat. No. 3,130,007 to Breck.

Various zeolites and zeolite-type materials are known in the art for the catalysis of chemical reactions. For example, U.S. Pat. No. 3,702,886, to Argauer, discloses a class of synthetic zeolites, characterized as "Zeolite ZSM-5", which are effective for the catalysis of various hydrocarbon conversion processes.

The zeolites suitable for the procedure of the invention can be in the basic form, in the partially or totally acidified form, or in the partially dealuminated form.

Preferably, the zeolite catalyst support in the process of the present invention are in the protic form, characterized as "H-ZSM-5" or "H-mordenite" zeolites, which are prepared from a corresponding "ZSM-5" zeolite or "mordenite" zeolite by replacing most, and generally at least about 80% of the cations of the latter zeolite with hydrogen ions using techniques well-known in the art. These zeolite catalysts are essentially crystalline aluminosilicates or in the neutral form, a combination of silica and alumina in a well defined crystalline structure. In a particularly preferred class of zeolite catalysts for purposes of the present invention, the molar ratio of $SiO_2$ to $Al_2O_3$ in these zeolites is within the ratio of about 10 to 60.

In another aspect of this invention, ruthenium is supported on either silica or iron oxide. A combination of ruthenium and tin, iron alone or a combination of platinum and iron, iron and cobalt, iron and ruthenium, and platinum and tin are supported on a high purity, low surface area silica or high purity, high surface area silica using the procedures well known in the art or the procedures further described herein. Other preferred catalyst supports for platinum or ruthenium based metal catalysts are titania and zirconia.

As noted above, the loading levels of a combination of two metal catalysts are generally referenced with the content of main catalyst metal and the weight ratio of the combination. For instance, the weight ratio of Ru/Sn, Ru/Fe, Pt/Sn or Pt/Fe is in the range of about 0.1 to 2. Thus, when the weight ratio of Ru/Sn, Ru/Fe or Pt/Fe is 0.1, the amount of ruthenium or platinum can be 0.1 or 1 weight percent and thus 1 or 10 weight percent of tin or iron is present on the catalyst support. Preferably, the weight ratio of Ru/Sn, Ru/Fe, Pt/Sn or Pt/Fe is about 0.5, and thus the amount of ruthenium or platinum on the catalyst support can be either 0.5 or 1 weight percent and that of tin or iron is either one or two weight percent. More preferably, the weight ratio of Ru/Sn, Ru/Fe, Pt/Sn or Pt/Fe is one or 0.2. Thus the amount of ruthenium or platinum on a support is 0.5, one or two weight percent and that of tin or iron is also 0.5, one or two weight percent when the weight ratio is one. Similarly, when a weight ratio of Ru/Sn, Ru/Fe or Pt/Fe is 0.2, the amount of ruthenium or platinum on the support can be 0.5 or one weight percent and of tin or iron is either 2.5 or five weight percent.

The amount of the third metal loading if present on a support is not very critical in this invention and can vary in the range of about 0.1 weight percent to about 10 weight percent. A metal loading of about 1 weight percent to about 6 weight percent based on the weight of the support is particularly preferred.

The metal impregnation can be carried out using any of the known methods in the art. Typically, before impregnation the supports are dried at 120° C. and shaped to particles having size distribution in the range of about 0.2 to 0.4 mm. Optionally, the supports may be pressed, crushed and sieved to a desired size distribution. Any of the known methods to shape the support materials into desired size distribution can be employed.

For supports having low surface area, such as, for example, alpha-alumina, the metal solutions are added in excess until complete wetness or excess liquid impregnation so as to obtain desirable metal loadings.

As noted above, the hydrogenation catalysts used in the process of this invention are generally bimetallic containing platinum/iron, ruthenium/tin, ruthenium/iron, iron/cobalt and so on. Generally, without intending to be bound by any theory, it is believed that one metal acts as a promoter metal and another metal is the main metal. For instance, in the instant process of the invention, of the above noted combinations respectively, platinum, ruthenium, and iron are considered as main metals for preparing hydrogenation catalysts of this invention. The other metals, tin with ruthenium and iron with cobalt, platinum or ruthenium are considered to be the promoter metals depending upon various reaction parameters including, but not limited to catalyst support employed, reaction temperature and pressure, etc. The catalysts may include other promoter metals, such as tungsten, vanadium, molybdenum, chromium or zinc.

The bimetallic catalysts are generally impregnated in two steps. Each impregnation step is followed by drying and calcination. The bimetallic catalysts may also be prepared by co-impregnation. In most cases, the impregnation may be carried out using metal nitrate solutions. However, various other soluble salts which upon calcinations release metal ions, can also be used. Examples of other suitable metal salts for impregnation include metal oxalate, metal hydroxide, metal oxide, metal acetate, ammonium metal oxide, such as ammonium heptamolybdate hexahydrate, metal acids, such as perrhenic acid solution, and the like.

Thus in one embodiment of this invention, there is provided a hydrogenation catalyst wherein the catalyst support is silica or iron oxide with ruthenium alone as the hydrogenation catalyst. In this aspect of the invention the metal loading of ruthenium can range from one (1) weight percent to about twenty (20) weight percent, preferably one to ten weight percent and most preferably one to five weight percent.

In another embodiment of this invention, there is provided a hydrogenation catalyst wherein the catalyst support is silica with iron alone as the hydrogenation catalyst. In this aspect of the invention the metal loading of iron can range from one (1) weight percent to about twenty (20) weight percent, preferably two to ten weight percent and most preferably three to eight weight percent of iron.

In another embodiment of this invention, there is provided a bimetallic loading of ruthenium and tin or platinum and tin. In this aspect of the invention, the loading of ruthenium or platinum is about 0.5 weight percent to about 2 weight percent and the loading of tin is about 2.5 weight percent to about 10 weight percent. Specifically, ruthenium/tin or platinum/tin loading levels of 1/1, 1/5, 0.5/5, and 0.5/2.5 weight percent on silica can be used.

In another embodiment of this invention, there is further provided a hydrogenation catalyst wherein the catalyst support is a high purity, low surface area silica with a bimetallic loading of platinum and iron or ruthenium and iron. In this aspect of the invention, the loading of platinum or ruthenium is about 0.5 weight percent to about 2 weight percent and the loading of iron is about 4 weight percent to about 10 weight percent. Specifically, platinum/iron or ruthenium/iron loading levels of 1/1, 1/5, 0.5/5, and 0.5/2.5 weight percent on high purity, low surface area silica can be used. Other preferred supports in this aspect of the invention include H-ZSM-5, graphitized carbon, zirconia, titania, iron oxide, silica-alumina and calcium silicate.

In another embodiment of this invention, there is further provided a hydrogenation catalyst wherein the bimetallic catalyst is cobalt and iron supported on silica. In this aspect of the invention, the loading level of cobalt is about 12 weight percent to about 22 weight percent and of iron is from about 3 to 8 weight percent. Specifically, cobalt loading level of 17.4 weight percent and iron loading level of 4.8 weight percent supported on silica is commercially available.

In general, by the practice of this invention, acetic acid can selectively be converted to acetaldehyde at very high rates. The selectivity to acetaldehyde in general is very high and may be at least 60 percent. Under preferred reaction conditions, acetic acid is converted to acetaldehyde at a selectivity of at least 70 percent or more preferably at a selectivity of over 80 percent such as at least 90 percent.

The conversion of acetic acid using the catalysts of this invention is at least 10% and can be up to 40% with selectivity to acetaldehyde at least 60%, preferably 70% and most preferably 80%.

Generally, the active catalysts of the invention are the single metal or the bimetallic catalysts as described herein. More specifically, a bimetallic catalyst containing ruthenium and tin, ruthenium and iron, platinum and tin, platinum and iron, and cobalt and iron supported on silica with a ruthenium or platinum loadings of 0.5 to 1 weight percent and tin and iron loadings of 5 weight percent and cobalt loading of about 18 weight percent are preferred. In accordance with the practice of this invention, acetic acid can be converted using this catalyst at conversions of around 40% with acetaldehyde selectivity of at least 60%, more preferably selectivity to acetaldehyde of at least 80% can be achieved.

Similar conversions and selectivities are achieved using zirconia, graphite or titania as a support and with similar loadings of ruthenium, platinum, tin, iron and cobalt as described above. Other promoter metals can also be used in conjunction with ruthenium or platinum as noted above.

In another aspect of this invention it is also possible to obtain high levels of conversions in the order of at least 25% and high selectivity to acetaldehyde of at least about 80% using ruthenium or iron loading of one weight percent to about five weight percent on silica or iron oxide as catalyst supports. In this aspect of the invention, other preferred catalyst supports include graphitized carbon, titania, zirconia, silica-alumina and calcium silicate.

In another aspect of the process of this invention, the hydrogenation is carried out at a pressure just sufficient to overcome the pressure drop across the catalytic bed.

The reaction may be carried out in the vapor or liquid state under a wide variety of conditions. Preferably, the reaction is carried out in the vapor phase. Reaction temperatures may be employed, for example in the range of about 250° C. to about 350° C., preferably about 290° C. to about 310° C. The pressure is generally uncritical to the reaction and subatmospheric, atmospheric or superatmospheric pressures may be employed. In most cases, however, the pressure of the reaction will be in the range of about 5 to 30 atmospheres absolute, most preferably the pressure of reaction zone is in the range of about 8 to 20 atmospheres absolute.

Although the reaction consumes a mole of hydrogen per mole of acetic acid to produce a mole of acetaldehyde, the actual molar ratio of acetic acid to hydrogen in the feed stream may be varied between wide limits, e.g. from about 100:1 to 1:100. It is preferred however, that such a ratio is in the range of about 1:20 to 1:2. More preferably, the molar ratio of acetic acid to hydrogen is about 1:5.

The raw materials used in connection with the process of this invention may be derived from any suitable source including natural gas, petroleum, coal, biomass and so forth. It is well known to produce acetic acid through methanol carbonylation, acetaldehyde oxidation, ethylene oxidation, oxidative fermentation, and anaerobic fermentation and so forth. As petroleum and natural gas have become more expensive, methods for producing acetic acid and intermediates such as methanol and carbon monoxide from alternate carbon sources have drawn more interest.

Of particular interest is the production of acetic acid from synthesis gas (syngas) that may be derived from any suitable carbon source. U.S. Pat. No. 6,232,352 to Vidalin, the disclosure of which is incorporated herein by reference, for example, teaches a method of retrofitting a methanol plant for the manufacture of acetic acid. By retrofitting a methanol plant the large capital costs associated with CO generation for a new acetic acid plant are significantly reduced or largely eliminated. All or part of the syngas is diverted from the methanol synthesis loop and supplied to a separator unit to recover CO and hydrogen, which are then used to produce acetic acid. In addition to acetic acid, the process can also be used to make hydrogen which is utilized in connection with this invention.

U.S. Pat. No. RE 35,377 to Steinberg et al., also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. See also, U.S. Pat. No. 5,821,111 to Grady et al., which discloses a process for converting waste biomass through gasification into synthesis gas as well as U.S. Pat. No. 6,685,754 to Kindig et al., the disclosures of which are incorporated herein by reference.

The acetic acid may be vaporized at the reaction temperature, and then it can be fed along with hydrogen in undiluted state or diluted with a relatively inert carrier gas, such as nitrogen, argon, helium, carbon dioxide and the like.

Alternatively, acetic acid in vapor form may be taken directly as crude product from the flash vessel of a methanol carbonylation unit of the class described in U.S. Pat. No. 6,657,078 to Scales et al., the disclosure of which is incorporated herein by reference. The crude vapor product may be fed directly to the reaction zones of the present invention without the need for condensing the acetic acid and light ends or removing water, saving overall processing costs.

Contact or residence time can also vary widely, depending upon such variables as the amount of acetic acid, catalyst, reactor, temperature and pressure. Typical contact times range from a fraction of a second to more than several hours when a catalyst system other than a fixed bed is used, with preferred contact times, at least for vapor phase reactions, between about 0.5 and 100 seconds.

Typically, the catalyst is employed in a fixed bed reactor e.g. in the shape of an elongated pipe or tube where the reactants, typically in the vapor form, are passed over or through the catalyst. Other reactors, such as fluid or ebullient bed reactors, can be employed, if desired. In some instances, it is advantageous to use the hydrogenation catalysts in conjunction with an inert material to regulate the pressure drop, flow, heat balance or other process parameters in the catalyst bed including the contact time of the reactant compounds with the catalyst particles.

In one of the preferred embodiments there is also provided a process for selective and direct formation of acetaldehyde from acetic acid comprising: contacting a feed stream containing acetic acid and hydrogen at an elevated temperature with a suitable hydrogenating catalyst containing about 0.5 weight percent to about 1 weight percent of platinum or ruthenium and about 2.5 weight percent to about 5 weight percent of tin or iron on a suitable catalyst support. Preferred catalyst support in this embodiment of the invention is silica.

In this embodiment of the process of this invention, the preferred hydrogenation catalyst contains about 0.5 weight percent or about one (1) weight percent platinum and about five (5) weight percent iron or tin; or about 0.5 weight percent or about one (1) weight percent ruthenium and about five (5) weight percent tin or iron. It is preferred that the hydrogenation catalysts are layered in a fixed bed and the reaction is carried out in the vapor phase using a feed stream of acetic acid and hydrogen in the molar range of about 1:20 to 1:5 and at a temperature in the range of about 290° C. to 310° C. and at a pressure of reaction zones in the range of about 8 to 20 atmospheres absolute, and the contact time of reactants is in the range of about 0.5 and 100 seconds.

Enriching of Acetaldehyde in the First Gaseous Product Stream:

In the second step of the process of this invention, the acetaldehyde formed in the first reaction zone, step (a) of the process of this invention as described herein is further enriched so as to result in a stream containing at least 50 mole percent of acetaldehyde. Any of the methods known in the art can be employed for this purpose. For example, one can employ a suitable distillation column to remove the volatile gaseous byproducts at the overhead and the bottom column to separate the high boiling fractions. Various other cryogenic methods and/or temperature controlled trapping devices can also be employed, such as a scrubbing column to remove either the impurities or other byproducts having either low or high boiling points such that the resulting stream contained at least 50 mole percent of acetaldehyde.

Preferably the enriched product stream from the first reaction zone contained at least 60 mole percent of acetaldehyde. More preferably the enriched gaseous product stream from the first reaction zone contained at least 70 mole percent of acetaldehyde. Even more preferably the enriched gaseous product stream from the first reaction zone contained at least 80 mole percent of acetaldehyde.

Reaction of Acetaldehyde with Acetic Anhydride to form Ethylidene Diacetate:

In one of the embodiments of the process of this invention the acetaldehyde formed in the first reaction zone can then be converted to VAM and actetic acid in one or more reactor zones by first reacting acetaldehyde with acetic anhydride to form ethylidene diacetate.

An example process for producing ethylidene diacetate utilizing acetaldehyde and acetic anhydride can be found in U.S. Pat. Nos. 3,700,722 and 3,383,374, both to McTeer, which describes the reaction of acetic anhydride and excess acetaldehyde at 25°-100° C., preferably 40°-60° C., in the presence of sulfuric acid to produce a mixture of ethylidene diacetate and bis(1-acetoxyethyl) ether after neutralizing the reaction with sodium hydroxide.

Thermal Decomposition of Ethylidene Diacetate:

Subsequent thermal decomposition of ethylidene diacetate generates VAM and acetic acid with the product stream containing VAM and acetic acid going to a separation unit. The thermal decomposition of ethylidene diacetate is typically carried out at a temperature between 50° and 200° C. at a pressure of less than 15 atm using a catalyst.

Examples of suitable acid catalysts useful for the thermal decomposition of ethylidene diacetate into VAM and acetic acid are aromatic sulfonic acids, sulfuric acid, and alkanesulfonic acids, see U.S. Pat. No. 2,425,389 to Oxley et al., U.S. Pat. No. 2,859,241 to Schnizer and U.S. Pat. No. 4,843,170 to Isshiki et al. In particular, benzene sulphonic acids, toluene sulphonic acids, ethylbenzene sulphonic acids, zylene sulphonic acids, and naphthalene sulphonic acids are preferred aromatic sulphonic acids.

In another embodiment, the separated acetic acid can be recycled back to the reactor system or drawn off to be purified as a final product.

Addition of Ketene to Acetaldehyde to form VAM:

In another embodiment of this invention, VAM can also be produced from the reaction of the acetaldehyde obtained in step (b) of the process of this invention and ketene. Ketene is commercially formed by the pyrolysis of acetic acid. Ketene so formed is then contacted with acetaldehyde formed in step (b) of the process of this invention.

Generally, the reaction of acetaldehyde with ketene maybe carried out in the vapor phase over a suitable acid catalyst. Any of the known solid acid catalysts maybe employed for this purpose. For instance, various acid catalysts as described hereinabove maybe suitable for this purpose. Typically, suitable solid acid catalysts include sulfonic acid resins such as perfluorosulfonic acid resins disclosed in U.S. Pat. No. 4,399,305 to Schreck, noted above. Zeolites are also suitable as solid acid catalysts as noted in U.S. Pat. No. 4,620,050 to Cognion et al. Thus, a zeolite catalyst may be used to concurrently support a hydrogenating catalyst as described hereinabove and then to react the resulting acetaldehyde with ketene to form VAM.

Thus in accordance with one aspect of the process of this invention there is also provided a consolidated fixed bed reactor wherein the front end of the reactor is loaded with the hydrogenation catalyst as described hereinabove, and the rear end of the reactor is loaded with a suitable acid catalyst as described hereinabove thereby both steps of one of the processes of this invention can effectively be carried out in a single stage. Any of the known fixed bed reactors that can bring about such results can be employed for this purpose. Preferably a tubular reactor designed to contain two different catalyst layers as described herein is employed to achieve this task.

Typically, reaction of acetaldehyde with ketene in the presence of a solid acid catalyst can be carried out in the temperature range of from about 150° C. to about 300° C., preferably in the range of from about 160° C. to about 250° C. and more preferably in the range of from about 170° C. to 225° C. Again, as described above any of the zeolites or sulfonic acid resin catalysts can be used as the solid acid catalyst. Preferably, this reaction is carried out in the presence of a zeolite having a pore diameter above about 0.6 nm. Specific examples of such zeolites include without any limitation mordenites, zeolite X and zeolite Y as described herein.

As noted above, another preferred acid catalyst that can be employed in this step of the process of this invention is perfluorosulfonic acid resin, which is commercially available under the trademark NAFION® from the DuPont de Nemours Company in Wilmington, Del. Suitable variations of these resins are described in U.S. Pat. No. 4,065,512 to Cares and in DuPont "Innovation," Volume 4, number 3, Spring 1973.

The following Examples A-O describe the procedures used for the preparation of various catalysts employed in Examples 1-19:

Example A

Preparation of 1 Weight Percent Ruthenium on Iron Oxide

Powdered and meshed iron oxide (99 g) of uniform particle size distribution of about 0.2 mm is dried at 120° C. in an oven under nitrogen atmosphere overnight and then cooled to room temperature. To this is added a solution of ruthenium nitrosyl nitrate (Heraeus) (3.14 g) in distilled water (32 ml). The resulting slurry is dried in an oven gradually heated to 110° C. (>2 hours, 10° C./min). The impregnated catalyst mixture is then calcined at 500° C. (6 hours, 1° C./min).

Example B

Preparation of 3 Weight Percent Ruthenium on Iron Oxide

The procedures of Example A are substantially repeated except for utilizing a solution of ruthenium nitrosyl nitrate (Heraeus) (9.42 g) in distilled water (96 ml) and 97 grams of iron oxide.

Example C

Preparation of 5 Weight Percent Iron on High Purity, Low Surface Area Silica

Powdered and meshed high purity, low surface area silica (95 g) of uniform particle size distribution of about 0.2 mm is dried at 120° C. in an oven under nitrogen atmosphere overnight and then cooled to room temperature. To this is added a solution of iron nitrate nonahydrate (Alfa Aesar) (36.2 g) in distilled water (36 ml). The resulting slurry is dried in an oven gradually heated to 110° C. (>2 hours, 10° C./min). The impregnated catalyst mixture is then calcined at 500° C. (6 hours, 1° C./min).

Example D

Preparation of 5 Weight Percent Tin and 0.5 Weight Percent Ruthenium on High Purity, Low Surface Area Silica Powdered and meshed high purity, low surface area silica (94 g) of uniform particle size distribution of about 0.2 mm is dried at 120° C. in an oven under nitrogen atmosphere overnight and then cooled to room temperature. To this is added a solution of tin oxalate (Alfa Aesar) (8.7 g) in dilute nitric acid (1N 45 ml). The resulting slurry is dried in an oven gradually heated to 110° C. (>2 hours, 10° C./min). The impregnated catalyst mixture is then calcined at 500° C. (6 hours, 1° C./min). To this calcined and cooled material is added a solution of 30 ruthenium nitrosyl nitrate (Heraeus) (1.57 g) in distilled water (16 ml). The resulting slurry is dried in an oven gradually heated to 110° C. (>2 hours, 10° C./min). The impregnated catalyst mixture is then calcined at 500° C. (6 hours, 1° C./min).

Example E

Preparation of 1 Weight Percent Ruthenium and 5 Weight Percent Iron on High Purity, Low Surface Area Silica Powdered and meshed high purity low surface area silica (94 g) of uniform particle size distribution of about 0.2 mm is dried at 120° C. in an oven under nitrogen atmosphere overnight and then cooled to room temperature. To this is added a solution of ruthenium nitrosyl nitrate (Heraeus) (3.14 g) in distilled water (32 ml). The resulting slurry is dried in an oven gradually heated to 110° C. (>2 hours, 10° C./min). The impregnated catalyst mixture is then calcined at 500° C. (6 hours, 1° C./min). To this calcined and cooled material is added a solution of iron nitrate nonahydrate (Alfa Aesar) (36.2 g) in distilled water (36 ml). The resulting slurry is dried in an oven gradually heated to 110° C. (>2 hours, 10° C./min). The impregnated catalyst mixture is then calcined at 500° C. (6 hours, 1° C./min).

Example F

Preparation of 5 Weight Percent Iron and 1 Weight Percent Platinum on High Purity, Low Surface Area Silica Powdered and meshed high purity, low surface area silica (94 g) of uniform particle size distribution of about 0.2 mm is dried at 120° C. in an oven under nitrogen atmosphere overnight and then cooled to room temperature. To this is added a solution of iron nitrate nonahydrate (Alfa Aesar) (36.2 g) in distilled water (36 ml). The resulting slurry is dried in an oven gradually heated to 110° C. (>2 hours, 10° C./min). The impregnated catalyst mixture is then calcined at 500° C. (6 hours, 1° C./min). To this calcined and cooled material is added a solution of platinum nitrate (Chempur) (1.64 g) in distilled water (16 ml). The resulting slurry is dried in an oven gradually heated to 110° C. (>2 hours, 10° C./min). The impregnated catalyst mixture is then calcined at 500° C. (6 hours, 1° C./min).

Example G

Preparation of 1 Weight Percent Platinum and 5 Weight Percent Tin on High Purity, Low Surface Area Silica Powdered and meshed high purity, low surface area silica (94 g) of uniform particle size distribution of about 0.2 mm is dried at 120° C. in an oven under nitrogen atmosphere overnight and then cooled to room temperature. To this is added a solution of platinum nitrate (Chempur) (1.64 g) in distilled water (16 ml) and a solution of tin oxalate (Alfa Aesar) (8.7 g) in dilute nitric acid (1N, 43.5 ml). The resulting slurry is dried in an oven gradually heated to 110° C. (>2 hours, 10° C./min.). The impregnated catalyst mixture is then calcined at 500° C. (6 hours, 1° C./min).

Example H

Preparation of 1 Weight Percent Palladium, 1 Weight Percent Gold and 5 Weight Percent Potassium Acetate on High Purity, Low Surface Area Silica The procedures of Example D are substantially repeated except for utilizing a solution of palladium nitrate (Heraeus) (2.17 g) in distilled water (22 ml), a solution of gold(III) hydroxide (Alfa Aesar) (1.26 g) and potassium hydroxide (0.28 g) in distilled water (10 ml), a solution of potassium acetate (Sigma) (5 g) in distilled water (10 ml) and 93 grams of silica. The catalyst is sequentially impregnated first with palladium and then with gold and finally with potassium acetate.

Example I

Preparation of 1 Weight Percent Palladium, 5 Weight Percent Copper and 5 Weight Percent Potassium Acetate on High Purity, Low Surface Area Silica The procedures of Example D are substantially repeated except for utilizing a solution of palladium nitrate (Heraeus) (2.17 g) in distilled water (22 ml), a solution of copper nitrate trihydrate (Alfa Aesar) (19 g) in distilled water (20 ml), a solution of potassium acetate (Sigma) (5 g) in distilled water (10 ml) and 89 grams of silica. The catalyst is sequentially impregnated first with copper and then with palladium and finally with potassium acetate.

Example J

Preparation of 1 Weight Percent Palladium and 5 Weight Percent Copper on Carbon The procedures of Example D are substantially repeated except for utilizing a solution of palladium nitrate (Heraeus) (2.17 g) in distilled water (22 ml), a solution of copper nitrate trihydrate (Alfa Aesar) (19 g) in distilled water (20 ml) and 94 grams of carbon. The catalyst is sequentially impregnated first with copper and then with palladium.

Example K

Preparation of 1 Weight Percent Palladium and 5 Weight Percent Iron on High Purity, Low Surface Area Silica The procedures of Example D are substantially repeated except for utilizing a solution of palladium nitrate (Heraeus) (2.17 g) in distilled water (22 ml), a solution of iron nitrate nonahydrate (Alfa Aesar) (36.2 g) in distilled water (30 ml) and 94 grams of silica. The catalyst is sequentially impregnated first with iron and then with palladium.

Example L

Preparation of 5 Weight Percent Iron and 5 Weight Percent Cobalt on High Purity, Low Surface Area Silica The procedures of Example D are substantially repeated except for utilizing a solution of iron nitrate nonahydrate (Alfa Aesar) (36.2 g) in distilled water (30 ml), a solution of cobalt nitrate hexahydrate (24.7 g) in distilled water (25 ml) and 90 grams of silica. The catalyst is sequentially impregnated first with iron and then with cobalt.

Example M

Preparation of 5 Weight Percent Copper and 5 Weight Percent Molybdenum on High Purity, Low Surface Area Silica The procedures of Example D are substantially repeated except for utilizing a solution of copper nitrate trihydrate (Alfa Aesar) (19 g) in distilled water (20 ml), a solution of ammonium heptamolybdate hexahydrate (Sigma) (9.5 g) in distilled water (65 ml) and 90 grams of silica. The catalyst is sequentially impregnated first with copper and then with molybdenum.

Example N

Preparation of 5 Weight Percent Tin and 1 Weight Percent Ruthenium on High Purity, Low Surface Area Silica The procedures of Example D are substantially repeated except for utilizing a solution of tin oxalate (Alfa Aesar) (8.7 g) in dilute nitric acid (1N, 43.5 ml), a solution of ruthenium nitrosyl nitrate (Heraeus) (3.14 g) in distilled water (32 ml) and 94 grams of silica. The catalyst is co-impregnated with tin and ruthenium.

Example O

Preparation of 1 Weight Percent Palladium on Iron Oxide

The procedures of Example D are substantially repeated except for utilizing a solution of palladium nitrate (Heraeus) (2.17 g) in distilled water (22 ml) and 99 grams of iron oxide.

Gas Chromatographic (GC) Analysis of the Products:

The analysis of the products was carried out by online GC. A three channel compact GC equipped with one flame ionization detector (FID) and 2 thermal conducting detectors (TCDs) was used to analyze the reactants and products. The front channel was equipped with a FID and a CP-Sil 5 (20 m)+WaxFFap (5 m) column and was used to quantify:

Acetaldehyde
Ethanol
Acetone
Methyl acetate
Vinyl acetate
Ethyl acetate
Acetic acid
Ethylene glycol diacetate
Ethylene glycol
Ethylidene diacetate
Paraldehyde The middle channel was equipped with a TCD and Porabond Q column and was used to quantify:

$CO_2$
Ethylene
Ethane

The back channel was equipped with a TCD and Molsieve 5A column and was used to quantify:

Helium
Hydrogen
Nitrogen
Methane
Carbon monoxide

Prior to reactions, the retention time of the different components was determined by spiking with individual compounds and the GCs were calibrated either with a calibration gas of known composition or with liquid solutions of known compositions. This allowed the determination of the response factors for the various components.

Examples 1-17 describe procedures for the hydrogenation of acetic acid to acetaldehyde as described in the first step of the process of the present invention.

Example 1

The catalyst utilized was 1 weight percent ruthenium on iron oxide prepared in accordance with the procedure of Example A.

In a tubular reactor made of stainless steel, having an internal diameter of 30 mm and capable of being raised to a controlled temperature, there are arranged 50 ml of 1 weight percent ruthenium supported on iron oxide. The length of the catalyst bed after charging was approximately about 70 mm. Prior to the reaction, the catalyst was reduced in situ by heating at a rate of 2° C./min to a final temperature of 400° C. Then, 5 mol % hydrogen in nitrogen was introduced to the catalyst chamber at a gas hourly space velocity (GHSV) of 7500 $h^{-1}$. After reduction, the catalyst was cooled to reaction temperature of 350° C. by continuing the gas flow of 5 mol % hydrogen in nitrogen. Once the reaction temperature was stabilized at 350° C., the hydrogenation of acetic acid was begun as follows:

A feed liquid was composed essentially of acetic acid. The reaction feed liquid was evaporated and charged to the reactor along with hydrogen and helium as a carrier gas with an average combined gas hourly space velocity (GHSV) of about 2500 $hr^{-1}$ at a temperature of about 350° C. The resulting feed stream contained a mole percent of acetic acid from about 4.4% to about 13.8% and the mole percent of hydrogen from about 14% to about 77%. A portion of the vapor effluent was passed through a gas chromatograph for analysis of the contents of the effluents. The selectivity to acetaldehyde was 60% at a conversion of acetic acid of 50%.

Example 2

The catalyst utilized was 5 weight percent iron on silica prepared in accordance with the procedure of Example C.

The procedure as set forth in Example 1 was substantially repeated with an average combined gas hourly space velocity (GHSV) of 2,500 $hr^{-1}$ of the feed stream of the vaporized acetic acid and hydrogen (H2 to acetic acid mole ratio of 5) at a temperature of 350° C. A portion of the vapor effluent is passed through a gas chromatograph for analysis of the contents of the effluents. The acetic acid conversion was 75% and acetaldehyde selectivity was 70%.

Example 3

The catalyst utilized was 0.5 weight percent ruthenium and 5 weight percent tin on silica prepared in accordance with the procedure of Example D.

The procedure as set forth in Example 1 is substantially repeated with an average combined gas hourly space velocity (GHSV) of 10,000 $hr^{-1}$ of the feed stream of the vaporized acetic acid and hydrogen ($H_2$ to acetic acid mole ratio of 5) at a temperature of 250° C. and at a pressure of 1 bar. A portion of the vapor effluent is passed through a gas chromatograph for analysis of the contents of the effluents. The acetic acid conversion was 4% and acetaldehyde selectivity was 91%. The other products formed were ethane (1%) and ethanol (8%).

Example 4

The catalyst utilized was 1 weight percent ruthenium and 5 weight percent iron on silica prepared in accordance with the procedure of Example E.

The procedure as set forth in Example 1 was substantially repeated with an average combined gas hourly space velocity (GHSV) of 2,500 $hr^{-1}$ of the feed stream of the vaporized acetic acid and hydrogen ($H_2$ to acetic acid mole ratio of 5) at a temperature of 300° C. A portion of the vapor effluent is passed through a gas chromatograph for analysis of the contents of the effluents. The acetic acid conversion is 35% and acetaldehyde selectivity is about 70%.

Example 5

The catalyst utilized was 1 weight percent platinum and 5 weight percent iron on High Purity, Low Surface Area Silica prepared in accordance with the procedure of Example F.

The procedure as set forth in Example 1 was substantially repeated with an average combined gas hourly space velocity (GHSV) of 2,500 $hr^{-1}$ of the feed stream of the vaporized acetic acid and hydrogen ($H_2$ to acetic acid mole ratio of 5) at a temperature of 350° C. and at a pressure of 1 bar. A portion of the vapor effluent is passed through a gas chromatograph for analysis of the contents of the effluents. The acetic acid conversion was 65% and acetaldehyde selectivity is 60%. The other products formed were carbon dioxide (6%) and ethyl acetate (9%).

Example 6

The catalyst utilized was 0.5 weight percent platinum and 5 weight percent tin on silica prepared in accordance with the procedure of Example G.

The procedure as set forth in Example 1 was substantially repeated with an average combined gas hourly space velocity (GHSV) of 2,500 hr$^{-1}$ of the feed stream of the vaporized acetic acid and hydrogen (H$_2$ to acetic acid mole ratio of 5) at a temperature of 350° C. and at a pressure of 1 bar. A portion of the vapor effluent is passed through a gas chromatograph for analysis of the contents of the effluents. The acetic acid conversion was 85% and acetaldehyde selectivity was 65%. The other products formed were methane (4%) and ethyl acetate (9%).

Example 7

The catalyst utilized was a commercially available Co/Fe catalyst containing 17.4 weight percent cobalt and 4.8 weight percent iron on silica The procedure as set forth in Example 1 is substantially repeated with an average combined gas hourly space velocity (GHSV) of 2,500 hr$^{-1}$ of the feed stream of the vaporized acetic acid and hydrogen at a temperature of 350° C. A portion of the vapor effluent is passed through a gas chromatograph for analysis of the contents of the effluents. The acetic acid conversion is about 65% and acetaldehyde selectivity is 75%.

Example 8

The catalyst utilized was 1 weight percent palladium, 1 weight percent gold and 5 weight percent potassium acetate on silica prepared in accordance with the procedure of Example H.

The procedure as set forth in Example 1 was substantially repeated with an average combined gas hourly space velocity (GHSV) of 10,000 hr$^{-1}$ of the feed stream of the vaporized acetic acid and hydrogen (H$_2$ to acetic acid mole ratio of 5) at a temperature of 250° C. and at a pressure of 1 bar. A portion of the vapor effluent is passed through a gas chromatograph for analysis of the contents of the effluents. The acetic acid conversion was 5% and acetaldehyde selectivity was 98.5%. The other products formed were ethane (1%) and ethanol (0.5%).

Example 9

The catalyst utilized was 1 weight percent palladium, 5 weight percent copper and 5 weight percent potassium acetate on silica prepared in accordance with the procedure of Example 1.

The procedure as set forth in Example 1 was substantially repeated with an average combined gas hourly space velocity (GHSV) of 10,000 hr$^{-1}$ of the feed stream of the vaporized acetic acid and hydrogen (H$_2$ to acetic acid mole ratio of 5) at a temperature of 250° C. and at a pressure of 1 bar. A portion of the vapor effluent is passed through a gas chromatograph for analysis of the contents of the effluents. The acetic acid conversion was 2% and acetaldehyde selectivity was 97.5%. The other product formed was ethane (2.5%).

Example 10

The catalyst utilized was 1 weight percent palladium and 5 weight percent copper on carbon prepared in accordance with the procedure of Example J.

The procedure as set forth in Example 1 was substantially repeated with an average combined gas hourly space velocity (GHSV) of 10,000 hr$^{-1}$ of the feed stream of the vaporized acetic acid and hydrogen (H$_2$ to acetic acid mole ratio of 5) at a temperature of 250° C. and at a pressure of 1 bar. A portion of the vapor effluent is passed through a gas chromatograph for analysis of the contents of the effluents. The acetic acid conversion was 1% and acetaldehyde selectivity was 97%. The other product formed was ethane (3%).

Example 11

The catalyst utilized was 1 weight percent palladium and 5 weight percent iron on silica prepared in accordance with the procedure of Example K.

The procedure as set forth in Example 1 was substantially repeated with an average combined gas hourly space velocity (GHSV) of 10,000 hr$^{-1}$ of the feed stream of the vaporized acetic acid and hydrogen (H$_2$ to acetic acid mole ratio of 5) at a temperature of 250° C. and at a pressure of 1 bar. A portion of the vapor effluent is passed through a gas chromatograph for analysis of the contents of the effluents. The acetic acid conversion was 9% and acetaldehyde selectivity was 96%. The other products formed were ethane (0.6%) and ethanol (3.6%).

Example 12

The catalyst utilized was 5 weight percent iron and 5 weight percent cobalt on silica prepared in accordance with the procedure of Example L.

The procedure as set forth in Example 1 was substantially repeated with an average combined gas hourly space velocity (GHSV) of 10,000 hr$^{-1}$ of the feed stream of the vaporized acetic acid and hydrogen (H$_2$ to acetic acid mole ratio of 5) at a temperature of 250° C. and at a pressure of 1 bar. A portion of the vapor effluent is passed through a gas chromatograph for analysis of the contents of the effluents. The acetic acid conversion was 11% and acetaldehyde selectivity was 95%. The other products formed were ethane (1%) and ethanol (4%).

Example 13

The catalyst utilized was 5 weight percent iron and 5 weight percent cobalt on silica prepared in accordance with the procedure of Example L.

The procedure as set forth in Example 1 was substantially repeated with an average combined gas hourly space velocity (GHSV) of 2,500 hr$^{-1}$ of the feed stream of the vaporized acetic acid and hydrogen (H$_2$ to acetic acid mole ratio of 5) at a temperature of 350° C. and at a pressure of 1 bar. A portion of the vapor effluent is passed through a gas chromatograph for analysis of the contents of the effluents. The acetic acid conversion was 75% and acetaldehyde selectivity was 70%. The other products formed were methane (4%) and carbon dioxide (3%).

Example 14

The catalyst utilized was 5 weight percent copper and 5 weight percent molybdenum on silica prepared in accordance with the procedure of Example M.

The procedure as set forth in Example 1 was substantially repeated with an average combined gas hourly space velocity (GHSV) of 2,500 hr$^{-1}$ of the feed stream of the vaporized acetic acid and hydrogen (H$_2$ to acetic acid mole ratio of 5) at a temperature of 350° C. and at a pressure of 1 bar. A portion of the vapor effluent is passed through a gas chromatograph for analysis of the contents of the effluents. The acetic acid conversion was 10% and acetaldehyde selectivity was 90%. The other products formed were ethane (1.5%) and acetone (6.6%).

Example 15

The catalyst utilized was 1 weight percent ruthenium and 5 weight percent tin on silica prepared in accordance with the procedure of Example N.

The procedure as set forth in Example 1 was substantially repeated with an average combined gas hourly space velocity (GHSV) of 2,500 hr$^{-1}$ of the feed stream of the vaporized acetic acid and hydrogen (H$_2$ to acetic acid mole ratio of 5) at a temperature of 350° C. and at a pressure of 1 bar. A portion of the vapor effluent is passed through a gas chromatograph for analysis of the contents of the effluents. The acetic acid conversion was 60% and acetaldehyde selectivity was 78%. The other products formed were methane (6%) and ethanol (12%).

Example 16

The catalyst utilized was 1 weight percent palladium on iron oxide prepared in accordance with the procedure of Example O.

The procedure as set forth in Example 1 was substantially repeated with an average combined gas hourly space velocity (GHSV) of 10,000 hr$^{-1}$ of the feed stream of the vaporized acetic acid and hydrogen (H$_2$ to acetic acid mole ratio of 5) at a temperature of 350° C. and at a pressure of 15 bar. A portion of the vapor effluent is passed through a gas chromatograph for analysis of the contents of the effluents. The acetic acid conversion was 66% and acetaldehyde selectivity was 59%. The other products formed were carbon dioxide (4%) and ethanol (18%).

Example 17

The catalyst utilized was commercially available copper-aluminum catalyst sold under the name of T-4489 from Sud Chemie.

The procedure as set forth in Example 1 was substantially repeated with an average combined gas hourly space velocity (GHSV) of 2,500 hr$^{-1}$ of the feed stream of the vaporized acetic acid and hydrogen (H$_2$ to acetic acid mole ratio of 5) at a temperature of 350° C. and at a pressure of 1 bar. A portion of the vapor effluent is passed through a gas chromatograph for analysis of the contents of the effluents. The acetic acid conversion was 88% and acetaldehyde selectivity was 51%. The other products formed were carbon dioxide (5%) and ethanol (16%).

Comparative Examples 1A-4A

These examples illustrate the reaction of acetic acid and hydrogen over a variety of catalysts wherein either no acetaldehyde was formed and/or very low selectivity to acetaldehyde was observed at low conversions of acetic acid.

In all of these examples, the procedure as set forth in Example 1 was substantially followed with the exception of using different catalysts as listed in Table 1. The reaction temperature and selectivity to acetaldehyde and other products are also tabulated in Table 1.

TABLE 1

Acetic Acid Conversion and Selectivities for Comparative Examples

| Example | Catalyst | Acetaldehyde selectivity (%) | Acetic acid conversion (%) | Other products |
|---------|----------|------------------------------|----------------------------|----------------|
| 1A | 5 wt % Cu/Fe$_2$O$_3$ | 31 | 100 | ethylene-16%, ethane-15%, ethyl acetate-4%, CO$_2$-5% |
| 2A | 5 wt % Co/H-ZSM-5 | 44 | 3 | ethylene-28%, ethane-28% |
| 3A | 5 wt % Co 5 Wt % Ru/SiO$_2$ | 78 | 4 | ethylene-14%, ethane-8% |
| 4A | 5 wt % Co/Carbon | 0 | 2 | Ethylene-12% acetone-8%, methane-47%, ethane-5% |

Example 18

To prepare the ethylidene diacetate of step (c), the enriched product feed stream containing essentially the acetaldehyde of step (b) is fed into a reactor with acetic anhydride to form a second product stream containing essentially ethylidene diacetate according to either one of U.S. Pat. No. 3,700,722 or 3,383,374, both to McTeer, which describes the reaction of acetic anhydride and excess acetaldehyde at 25°-100° C., (preferably 40°-60° C.) in the presence of sulfuric acid.

Example 19 describes the thermal decomposition of ethylidene diacetate into VAM and acetic acid as described in step (d) of the present invention. The procedure as set forth in U.S. Pat. No. 4,843,170 to Isshiki et al is used to thermally decompose the ethylidene diacetate formed in step (c) of the present invention utilizing any one of the Examples 1-17 to produce acetaldehyde which is reacted with the acetic anhydride in step (c) of the present invention. The thermal decomposition of said ethylidene diacetate typically occurs at a temperature between 50° and 200° C. and a pressure of less than 15 atm.

Example 19

Any one of the catalyst prepared according to Examples A-O can be used in the procedure as set forth in U.S. Pat. No. 5,719,315 to Tustin et al to carry out the final step of the production of VAM from the reaction of the acetaldehyde formed in step (b) and a ketene with an acid catalyst.

While the invention has been illustrated in connection with particular examples, modifications to these examples within the spirit and scope of the invention will be readily apparent to those of skill in the art. In view of the foregoing discussion, relevant knowledge in the art and references discussed above in connection with the Background and Detailed Description, the disclosures of which are all incorporated herein by reference, further description is deemed unnecessary.

What is claimed is:

1. A process for the production of vinyl acetate from acetic acid comprising:
 a. contacting in a first reaction zone a feed stream containing acetic acid and hydrogen at an elevated temperature with a suitable hydrogenating catalyst carried on a suitable catalyst support to form a first gaseous product stream comprising acetaldehyde, wherein said hydrogenating catalyst further comprises a first metal comprising from 0.5 to 1.0 wt. % of palladium and a second metal selected from the group consisting of iron, copper, gold, potassium and combinations thereof;

b. enriching said first gaseous product stream with acetaldehyde at least 50 mole percent;

c. contacting in a second reaction zone said enriched first gaseous product stream obtained in step (b) at an elevated temperature with acetic anhydride to form a second gaseous product stream of ethylidene diacetate;

d. thermally decomposing in a third reaction zone said second gaseous product stream obtained in step (c) with a suitable acid catalyst to form a third gaseous product stream comprising a mixture of vinyl acetate and acetic acid;

e. separating the vinyl acetate from said third gaseous product stream.

2. The process according to claim 1, wherein the catalyst support in step (a) is selected from the group consisting of silica, alumina, silica-alumina, calcium silicate, zirconia, titania and combinations thereof.

3. The process according to claim 1, wherein step (c) further comprises contacting with a catalyst that is selected from the group consisting of platinum supported on alumina or silica and ruthenium supported on alumina or silica.

4. The process according to claim 1, wherein the first gaseous product stream is enriched with acetaldehyde at least up to 80 mole percent in step (b).

5. The process according to claim 1, wherein the reactants in step (a) consist of acetic acid and hydrogen with a molar ratio in the range of about 100:1 to 1:100, the temperature of the reaction zones are in the range of about 250° C. to 350° C., and the pressure of the reaction zones are in the range of about 5 to 25 atmospheres absolute.

6. The process according to claim 1, wherein the reactants in step (a) consist of acetic acid and hydrogen with a molar ratio in the range of about 1:20 to 1:2 the temperature of the reaction zones are in the range of about 270° C. to 310° C., and the pressure of the reaction zones are in the range of about 8 to 20 atmospheres absolute.

7. The process according to claim 1, wherein the second metal loading level of the hydrogenation catalyst in step (a) is from about 0.5 to about 20 weight percent.

8. The process according to claim 1, wherein the acid catalyst in step (d) is selected from aromatic sulfonic acids, sulfuric acid, and alkane sulfonic acids.

* * * * *